United States Patent
Teng et al.

(10) Patent No.: US 10,456,383 B2
(45) Date of Patent: Oct. 29, 2019

(54) TARGETED APPROACH IN THE MANAGEMENT OF EPIDERMOLYSIS BULLOSA

(71) Applicant: The Board of Trustees of the Leland Stanford Junior University, Stanford, CA (US)

(72) Inventors: Joyce Teng, Stanford, CA (US); Heather Irina Rishel, San Francisco, CA (US); Dédée F. Murrell, Sydney (AU)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/994,094

(22) Filed: May 31, 2018

(65) Prior Publication Data

US 2018/0344707 A1    Dec. 6, 2018

Related U.S. Application Data

(60) Provisional application No. 62/513,876, filed on Jun. 1, 2017.

(51) Int. Cl.
| | | |
|---|---|---|
| *A61K 31/436* | (2006.01) | |
| *A61P 17/02* | (2006.01) | |
| *A61K 9/00* | (2006.01) | |
| *A61K 9/06* | (2006.01) | |

(52) U.S. Cl.
CPC .......... *A61K 31/436* (2013.01); *A61K 9/0014* (2013.01); *A61P 17/02* (2018.01)

(58) Field of Classification Search
CPC ...... A61K 31/436; A61K 9/0014; A61K 9/06; A61P 17/02
See application file for complete search history.

(56) References Cited

U.S. PATENT DOCUMENTS

| 5,286,730 A * | 2/1994 | Caufield | A61K 31/70 514/291 |
| 2013/0225630 A1 | 8/2013 | Teng et al. | |
| 2016/0184279 A1 * | 6/2016 | Kaspar | A61K 47/10 514/291 |

OTHER PUBLICATIONS

Huang, Anticancer Agents Med Chem Sep. 2013, 13(7), 967-970 (Year: 2013).*
Fogel, J AM Acad Dermatol, 72, 5, p. 879-889 (Year: 2015).*
Zheng et al, Mol Cell Pharmacol, 2015, 7(2), 15-20 (Year: 2015).*
Dill, Pediatric Neurology, 51, 2014, 109-113 (Year: 2014).*
Fine et al. (J Am Acad Dermatology, 2014, 70, 1103-26). (Year: 2014).*
Loh et al. (J Am Dermatol 2014, 70, 89-97). (Year: 2014).*
Hickerson et al., "Rapamycin selectively inhibits expression of an inducible keratin (K6a) in human keratinocytes and improves symptoms in pachyonychia congenita patients", J Dermatol Sci., Nov. 2009, pp. 82-88, vol. 56, Issue 2, Elsevier, New York City, NY.
Fogel et al., "Advances in the therapeutic use of mammalian target of rapamycin (mTOR) inhibitors in dermatology", J Am Acad Dermatol., May 2015, pp. 879-889, 72(5), American Academy of Dermatology, Inc., Washington, D.C.

* cited by examiner

*Primary Examiner* — Umamaheswari Ramachandran
(74) *Attorney, Agent, or Firm* — Pamela J. Sherwood; Bozicevic, Field & Francis LLP

(57) ABSTRACT

Methods are provided for the targeted treatment of Epidermolysis Bullosa simplex.

12 Claims, No Drawings

TARGETED APPROACH IN THE MANAGEMENT OF EPIDERMOLYSIS BULLOSA

CROSS REFERENCE

This application claims benefit of U.S. Provisional Patent Application No. 62/513,876, filed Jun. 1, 2017, which application is incorporated herein by reference in its entirety.

BACKGROUND

Epidermolysis bullosa (EB) represents a spectrum of conditions characterized by blistering and mechanical fragility of the skin. Individuals with EB display tremendous clinical diversity, as the dermal-epidermal basement membrane zone contains a number of specialized adhesive structures which links the basal epidermis cytoskeleton to the papillary dermis. The molecular basis of EB has been linked to 18 genes, leading to the classification of 28 clinical (15 EBS, 8 JEB, 14 DEB, 1 Kindler) EB subtypes and four major EB groups (Fine et al., JAAD June 2014). The EB simplex (EBS) subtype has been well-characterized genetically.

EBS refers to a group of rare genetic disorders caused by blister formation within the epidermis. The clinical features of all forms of EBS manifest with skin blistering. Palmo-plantar-keratoderma, nail dystrophy and shedding, alopecia and oral involvement are often seen. Excruciating pain and severe impairment in quality of life in EBS patients have been reported (Fine et al., JAAD June 2014; Horn and Tidman, Clin Exp Dermatol 2002).

Causes of early mortality in EBS patients include infections and protein loss leading to malnutrition, fluid and electrolyte imbalances, and anemia. Patient care has been limited to supportive measures, including wound care, nutritional support, and antibiotics. In 1991, two groups published in Cell and Science independently revealing the first keratin disorder with a genetic basis in humans, EBS. EBS is usually caused by missense mutations in the genes encoding keratin 5 and 14 (KRT5 and KRT14, respectively) leading to a dominant negative effect on the function of normal keratins (Lane et al., J Pathol 2004), resulting in keratin cytoskeleton dysfunction. The prevalence is estimated to be 6 to 30 per 1 million live births (Horn et al., BJD 1997; Fine et al., JAAD 1991; McKenna et al., BJD 1992).

Targeted methods to ease the symptoms of EB are of great clinical interest, and are provided herein.

SUMMARY

Compositions and methods are provided for the targeted treatment of Epidermolysis Bullosa simplex (EBS) plantar lesions in a human subject. An effective dose of a pharmaceutical formulation comprising an inhibitor of mTOR is topically applied to the lesions, with a periodicity and for a time sufficient to ameliorate the severity of EBS. Without being bound by the theory of activity, it is believed that the mTOR inhibitor down regulates translation of defective K5 and/or K14 keratin proteins that cause EBS. In some embodiments the keratin protein is K5. Additionally the mTOR inhibitor may inhibit rapid proliferation of cells carrying defective keratin, directly ameliorating pain and itch in the treated surface.

In some embodiments the mTOR inhibitor is a rapamycin macrolide. In some embodiments the rapamycin macrolide is Sirolimus (rapamycin). The mTOR inhibitor is topically administered in a pharmaceutically acceptable excipient, e.g. ointment, cream, gel, lotion, and the like. The formulation may be a non-aqueous ointment, cream, lotion or liposome. The formulation may comprise a dose of mTOR inhibitor equivalent to from about 0.1 to about 10% weight/volume rapamycin, e.g. from 0.1% to about 5%; or about 0.5% rapamycin by weight/vol., about 1% rapamycin, about 2% rapamycin, about 3% rapamycin, about 4% rapamycin, about 5% rapamycin, or more. Administration may be daily, twice daily, thrice daily, etc. In other embodiments a sustained delivery patch can be provided for continuous delivery of the agent.

DETAILED DESCRIPTION

It is to be understood that this invention is not limited to the particular methodology, protocols, cell lines, animal species or genera, and reagents described, as such may vary. It is also to be understood that the terminology used herein is for the purpose of describing particular embodiments only and is not intended to limit the scope of the present invention, which will be limited only by the appended claims.

As used herein, the singular forms "a," "an," and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Any embodiment of any of the present methods, devices, and systems may consist of, or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only, or the alternatives are mutually exclusive, although the disclosure supports a definition that refers to only alternatives and "and/or."

Throughout this application, the term "about" is used to indicate that a value includes the standard deviation of error for the device or method being employed to determine the value.

mTOR pathway. The mammalian target of rapamycin (mTOR) is one of a family of proteins involved in cell cycle progression, DNA recombination, and DNA damage detection. The cDNA for mTOR encodes a predicted 2,549-amino acid protein with a molecular mass of approximately 300 kD. Inhibitors of the mTOR pathway include, without limitation, rapamycin and related compounds.

The macrolide fungicide rapamycin is a natural product that binds intracellularly to the immunophilin FK506 binding protein 12 (FKBP12), and the resultant complex inhibits the serine protein kinase activity of mammalian target of rapamycin (mTOR). The inhibition of mTOR, in turn, blocks signals to at least two separate downstream pathways which control the translation of specific mRNAs required for cell proliferation, including Otubain1. Related mTOR inhibitors include, without limitation, any of the rapamycin macrolides, e.g. rapamycin, CCI-779, Everolimus, and ABT-578.

Wherever the present application refers to "rapamycin macrolide", in addition to naturally occurring forms of rapamycin, the invention further includes rapamycin analogs and derivatives. Many such analogs and derivatives are known in the art. Examples include those compounds described in U.S. Pat. Nos. 6,329,386; 6,200,985; 6,117,863; 6,015,815; 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; and 5,023,262; all of which are incorporated herein by reference.

Desirable rapamycin macrolides for use in the present methods include rapamycin, CCI-779, Everolimus (also known as RAD001), and ABT-578. CCI-779 is an ester of rapamycin (42-ester with 3-hydroxy-2-hydroxymethyl-2-methylpropionic acid), disclosed in U.S. Pat. No. 5,362,718. Everolimus is an alkylated rapamycin (40-O-(2-hydroxyethyl)-rapamycin, disclosed in U.S. Pat. No. 5,665,772.

Rapamycin (Sirolimus) is a natural macrocyclic lactone produced by the bacterium *Streptomyces hygroscopicus*, with immunosuppressant properties. Sirolimus has shown to decrease overall protein synthesis by 20% and cause cell cycle arrest in G1 phase. Other effects of sirolimus include apoptosis, inhibition of T-cell activation and reduced expression of specific proteins involved in angiogenesis and lymphangiogenesis, specifically hypoxia inducible factor-1a (HIF-1a) and vascular endothelial growth factor (VEGF).

Systemic use of sirolimus is associated with side effects that include opportunistic infection, mucositis, hypercholesterolemia, decreased renal function, elevation in liver transaminases, thrombocytopenia, neutropenia, and delayed wound healing. Minor adverse cutaneous events of systemic therapy include acne like eruptions, oedema, and nail disorders. mTOR inhibitors in topical preparations show promise as an ideal delivery system to minimize systemic adverse effects in the treatment of dermatological disease.

Topical sirolimus has been used off-label in a variety of dermatological diseases. Formulations are mostly crushed rapamycin from tablet compounded with petrolatum to form an ointment, with a few studies utilizing the commercially available oral rapamycin solution (1 mg/ml). Most of the topical formulations were found to have no local adverse effects, with irritation being more common using the aqueous solution. In all cases the systemic level of rapamycin was less than 2 ng/ml which is below the standard serum levels required for immunosuppression (5-15 ng/ml). Treatment duration and frequency varied according to condition.

Keratin 5, also known as KRT5, K5, or CK5, is a protein that is encoded in humans by the KRT5 gene. It dimerizes with keratin 14 and forms the intermediate filaments (IF) that make up the cytoskeleton of basal epithelial cells. This protein is involved in several diseases including epidermolysis bullosa simplex. Keratin 14 also known as cytokeratin-14 (CK-14) or keratin-14 (KRT14) is a member of the type I keratin family of intermediate filament proteins encoded by the KRT14 gene.

Keratin 5 and K14 are expressed primarily in basal keratinocytes in the epidermis, specifically in the stratified epithelium lining the skin and digestive tract. Keratin intermediate filaments make up the cytoskeletal scaffold within epithelial cells, which contributes to the cell architecture and provides the cells with the ability to withstand mechanical, and non-mechanical, stresses. K5/K14 keratin pairs are able to undergo extensive bundling due to the non-helical tail of K15 acting as a weak cross-linker at the intermediate filament surface. This bundling increases the elasticity, and therefore the mechanical resilience, of the intermediate filaments. K5/K14 intermediate filaments are anchored to the desmosomes of basal cells via desmoplakin and plakophilin-1.

Epidermolysis bullosa simplex (EBS) is a group of rare predominantly autosomal dominant genetic skin diseases affecting approximately 1:25000-50 000 live births of the population. In EBS, two major subtypes have been defined: suprabasal and basal EBS. The basal types are associated with keratin mutations. EBS is the most common subtype of EB with clinical manifestations usually present at birth, characterized by intra-epidermal blistering due to cell degeneration within the basal layer of the epidermis and often with involvement of mucosal epithelia. Blistering is associated with mechanical stress and the blisters tend to heal without scarring.

EBS is usually caused by mutations in keratin KRT5 or KRT14, and the pathogenic mutations usually occur within regions of the keratin genes that encode "hotspots" in the protein structure, namely the H1 domain of the head region (only for type II keratins), two segments (1A and 2B) of the rod domain, and the central linker region L12. Examples of known mutations in K5 and K14 may be found in public databases, for example interfil.org. More than one-third of EBS-DM cases are caused by a unique mutation in the KRT14 gene that affecting a highly conserved arginine (Arg125) located within the HIP of K14, a known "hot spot" that is most likely due to a conserved hypermutable CpG dinucleotide in all type I keratins. Here, the cysteine (TGC) or histidine (CAC) often substituted for arginine codon (CGC) when mutated.

In EBS, genotype—phenotype correlations are quite well established. In the majority of cases the clinical severity relates to the location of the mutations and the degree to which these mutations perturb keratin structural assembly. Generally, six mutation hotspots are known to exist: mutations in EBS-DM are generally restricted to the helix boundary peptides of K5 and K14 which mark the importance of these structures for KIF assembly and elongation. In milder forms of EBS, the underlying mutations occur outside the helix boundary motifs, namely the H1 domain of K5, the second half of the 1A domain, the L12 domain and the central 2B domain of both proteins. Since such mutations do not interfere with the elongation process during filament assembly, ultrastructural examination reveals apparently normal filament, but consists of structurally weakened filaments that break upon mild mechanical stress. Conservative amino acid changes in the helix boundary motifs as well as complete disintegration of the amino acid sequences by frame shift mutations may also result in milder disease phenotypes. Thus, based on the location of a mutation in K5 and K14 one can possibly predict the resulting phenotype.

Although EBS is generally transmitted in an autosomal dominant mode, about 5% of EBS cases have been identified with inherited recessive mutations. More than 10 different KRT14 mutations have been associated with recessive EBS (EBS-AR) including nonsense mutations, missense mutations, splice site mutations, deletion and deletion/insertion mutations. In some cases of recessive EBS, compound heterozygous mutations have been described in K5.

Upon mild physical trauma, the keratin filament network is easily compromised, resulting in structural failure of the affected epithelial keratinocytes and loss of tissue integrity. The degree of severity of the clinical phenotype has been directly linked to the position of the pathogenic mutation along the keratin polypeptide backbone, although more recent reports provide some exceptions to this, whereby also milder disease phenotypes are caused by pathogenic mutations in the conserved hot spot region of the KRT genes. However, other additional factors may as well affect and exacerbate disease severity. Based on the clinical severity, recent reclassification distinguishes four major EBS subgroups: a) the generalized Dowling-Meara EBS (EBS-DM; OMIM 131760), b) other generalized non-DM EBS (gen non-DM EBS; OMIM 131900), c) the localized EBS (EBS-Loc; OMIM 131800) and d) EBS with mottled pigmentation (EBS-MP; OMIM 131960).

In both generalized forms, the most severe Dowling-Meara subtype and the milder non-Dowling-Meara subtype, also previously known as the Koebner form, present generalized and pronounced blistering at birth, while the localized EBS is milder with blistering confined to palmar and plantar regions of the body. Nevertheless, other not yet identified genetic or epigenetic modifiers and environmental factors, such as patient lifestyle and climate condition, clearly influence the phenotypic expression as different subtypes of EBS have been associated with the same mutation in several instances.

The generalized Dowling-Meara subtype (EBS-DM) is the most severe form being manifested at birth with erythema, widespread blistering, erosions and areas of denuded skin presenting spontaneous clusters of blisters also called "herpetiform" at multiple sites of the body which improves with age. Progressive palmoplantar keratoderma becomes the chief complaint in adulthood. Other hallmarks include callosite formation, secondary bacterial infections and sepsis, involvement of mucous membranes, nail dystrophy, healing of lesions without scarring and involvement of the oral mucosa. Inflammation especially of haemorrhagic blisters may be followed by transient milia formation, as well as healing of skin with hypo- and hyperpigmentation. Diagnostic criteria include ultrastructural examination of skin biopsies showing the characteristic clumps or electron dense aggregates composed of K5 and K14 KIFs protein in the cytoplasm of basal keratinocytes harboring the mutation.

The generalized non-DM EBS (gen-non-DM EBS), is a more moderate subtype characterized at birth or in early infancy by generalized blistering, without clustering. The clinical presentation in majority of the cases is moderate, without any extra-cutaneous involvement, but with palms, soles and extremities being mostly affected and often in response to minor trauma and induced by increased ambient temperature. The disease-associated mutations in the gen non-DM EBS are more centrally located in the rod domain and sometimes more widely distributed along both KRT5 and KRT14 genes, including the non-helical linker segments.

The localized EBS (EBS-loc), a clinically mild phenotype and the commonest form previously known as EBS-Weber Cockayne (EBS-WC), is characterized by late appearing skin blistering restricted to areas of greater friction or trauma such as hands and feet. Children tend not to be affected until they start to walk or crawl and the blistering worsens with warm humid weather. Secondary infections of blistering lesions on the feet are the most common complication. Some affected individuals suffer from focal keratoderma (thickening of the skin of hands and feet).

The term "genotype" with respect to a particular gene refers to a sum of the alleles of the gene contained in an individual or a sample.

The terms "determining the genotype" of a K5/K14 gene refers to determining the polymorphisms present in the individual alleles of the K5/K14 gene present in a subject.

The terms "target region" or "target sequence" refer to a polynucleotide sequence to be studied in a sample. In the context of the present invention, the target sequences are the K5/K14 gene sequences contained in the sample from an individual.

The term "oligonucleotide" refers to a short nucleic acid, typically ten or more nucleotides in length. Oligonucleotides are prepared by any suitable method known in the art, for example, direct chemical synthesis as described in Narang et al. (1979) *Meth. Enzymol.* 68:90-99; Brown et al. (1979) *Meth. Enzymol.* 68:109-151; Beaucage et al. (1981) *Tetrahedron Lett.* 22:1859-1862; Matteucci et al. (1981) *J. Am. Chem. Soc.* 103:3185-3191; or any other method known in the art.

The term "primer" refers to an oligonucleotide, which is capable of acting as a point of initiation of nucleic acid synthesis along a complementary strand of a template nucleic acid. A primer that is at least partially complementary to a subsequence of a template nucleic acid is typically sufficient to hybridize with template nucleic acid and for extension to occur. Although other primer lengths are optionally utilized, primers typically comprise hybridizing regions that range from about 6 to about 100 nucleotides in length and most commonly between 15 and 35 nucleotides in length. The design of suitable primers for the amplification of a given target sequence is well known in the art and described in the literature cited herein. The design of suitable primers for parallel clonal amplification and sequencing is described e.g. in a U.S. Application Pub. No. 20100086914.

A "thermostable nucleic acid polymerase" or "thermostable polymerase" is a polymerase enzyme, which is relatively stable at elevated temperatures when compared, for example, to polymerases from *E. coli*. As used herein, a thermostable polymerase is suitable for use under temperature cycling conditions typical of the polymerase chain reaction ("PCR").

The terms "nucleic acid" refers to polymers of nucleotides (e.g., ribonucleotides and deoxyribonucleotides, both natural and non-natural) such polymers being DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non-natural bases. The example of non-natural bases include those described in, e.g., Seela et al. (1999) *Helv. Chim. Acta* 82:1640. Certain bases used in nucleotide analogs act as melting temperature ($T_m$) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

The term "sample" refers to any composition containing or presumed to contain nucleic acid from an individual. The sample can be obtained by any means known to those of skill in the art. Such sample can be an amount of tissue or fluid, or a purified fraction thereof, isolated from an individual or individuals, including tissue or fluid, for example, skin, plasma, serum, whole blood and blood components, spinal fluid, saliva, peritoneal fluid, lymphatic fluid, aqueous or vitreous humor, synovial fluid, urine, tears, seminal fluid, vaginal fluids, pulmonary effusion, serosal fluid, organs, bronchio-alveolar lavage, tumors and paraffin embedded tissues. Samples also may include constituents and components of in vitro cultures of cells obtained from an individual, including, but not limited to, conditioned medium resulting from the growth of cells in the cell culture medium, recombinant cells and cell components.

Therapeutic Treatment Methods

As used herein, the term "treating" is used to refer to treatment of pre-existing EBS, particularly plantar's lesions, such as blisters, erythema, etc. The formulations of the invention are used to treat ongoing disease, by stabilizing or improving the clinical symptoms of the patient.

The dose will vary depending on the specific compound utilized, specific disorder, patient status, etc. Typically a therapeutic dose will be sufficient to substantially decrease the blistering, erythema, etc. afflicting the subject. The individual may be monitored for improvement on one or more indicia. Indicia of effectiveness may include foot function utilizing the validated Foot Health Status Questionnaire (FHSQ) as a change from baseline to the end of each treatment; a decrease in plantar defect size measurements; a change in EB Disease Activity and Scarring Index (EB-DASI) feet activity scores; improved quality of life assessment in EB (QOLEB); reduced itch severity; increased mobility; changes in foot plantar pressure measurements; and mTOR pathway inhibition.

An individual suffering from EBS is optionally analyzed for genotype to confirm that a mutation in one or both of K5 and K14 is present. Sequence analysis can be used to detect specific polymorphisms in a K5/K14 nucleic acid. A test sample of DNA or RNA is obtained from the test individual. PCR or other appropriate methods can be used to amplify the gene or nucleic acid, and/or its flanking sequences, if desired. The sequence of a K5/K14 nucleic acid, or a fragment of the nucleic acid, or cDNA, or fragment of the cDNA, or mRNA, or fragment of the mRNA, is determined, using standard methods. The sequence of the nucleic acid, nucleic acid fragment, cDNA, cDNA fragment, mRNA, or mRNA fragment is compared with the known nucleic acid sequence of the gene or cDNA or mRNA, as appropriate. The presence of a polymorphism indicated herein as being associated with EBS in the K5/K14 gene indicates that the individual may be treated with the methods of the invention.

Allele-specific oligonucleotides can also be used to detect the presence of a polymorphism in a K5/K14 nucleic acid, through the use of dot-blot hybridization of amplified oligonucleotides with allele-specific oligonucleotide (ASO) probes (see, for example, Saiki, R. et al., Nature 324:163-166 (1986)). An "allele-specific oligonucleotide" (also referred to herein as an "allele-specific oligonucleotide probe") is an oligonucleotide of approximately 10-50 base pairs that specifically hybridizes to a K5/K14 nucleic acid, and that contains a polymorphism of interest. An allele-specific oligonucleotide probe that is specific for particular polymorphisms in a K5/K14 nucleic acid can be prepared, using standard methods (see Current Protocols in Molecular Biology).

In another aspect, arrays of oligonucleotide probes that are complementary to target nucleic acid sequence segments from an individual can be used to identify the presence of polymorphic alleles in a K5/K14 nucleic acid. For example, in one aspect, an oligonucleotide array can be used. Oligonucleotide arrays typically comprise a plurality of different oligonucleotide probes that are coupled to a surface of a substrate in different known locations. These oligonucleotide arrays, also described as "Genechips™," have been generally described in the art, for example, U.S. Pat. No. 5,143,854 and PCT patent publication Nos. WO 90/15070 and 92/10092.

In another aspect of the invention, expression and/or composition of a K5/K14 polypeptide can be examined, by a variety of methods, including enzyme linked immunosorbent assays (ELISAs), Western blots, immunoprecipitations and immunofluorescence. A test sample from an individual is assessed for the presence of an alteration in the expression and/or an alteration in composition of the polypeptide encoded by a K5/K14 nucleic acid, or for the presence of a particular variant encoded by a K5/K14 nucleic acid. An alteration in expression of a polypeptide encoded by a K5/K14 nucleic acid can be, for example, an alteration in the quantitative polypeptide expression (i.e., the amount of polypeptide produced); an alteration in the composition of a polypeptide encoded by a K5/K14 nucleic acid is an alteration in the qualitative polypeptide expression (e.g., expression of an altered K5/K14 polypeptide or of a different splicing variant). In a preferred aspect, diagnosis of a susceptibility to type 2 diabetes can be made by detecting a particular splicing variant encoded by that K5/K14 nucleic acid, or a particular pattern of splicing variants.

Pharmaceutical Compositions mTOR inhibitors and combinations of inhibitors can serve as the active ingredient in pharmaceutical compositions formulated for the topical treatment of lesions associated with EBS. The compositions can also include various other agents to enhance delivery and efficacy. For instance, compositions can include agents capable of increasing the bioavailability of the compound. The compositions can also include various agents to enhance delivery and stability of the active ingredients.

Thus, for example, the compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. Examples of such modifications or complexing agents include sulfate, gluconate, citrate and phosphate.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions described herein can be administered in a variety of different ways, usually topically.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The therapeutic compositions for use in the methods of the invention preferably include a pharmaceutically acceptable carrier that provides the medium in which are dissolved or suspended the constituents of the compositions. Suitable carriers include any medium, oil, emulsion, ointment and the like that will allow the therapeutic compositions to be delivered to the target wound without increasing damage to the tissues of the wound.

Medical dressings suitable for use in the methods of the present invention for contacting a wound with the therapeutic compositions can be any material that is biologically acceptable and suitable for placing over any chronic wound. In exemplary embodiments, the support may be a woven or non-woven fabric of synthetic or non-synthetic fibers, or any combination thereof. The dressing may also comprise a support, such as a polymer foam, a natural or man-made sponge, a gel or a membrane that may absorb or have disposed thereon, a therapeutic composition.

In some embodiments, the formulation comprises permeation enhancer, e.g. transcutol, (diethylene glycol monoethyl ether), propylene glycol, dimethylsulfoxide (DMSO), menthol, 1-dodecylazepan-2-one (Azone), 2-nonyl-1,3-dioxolane (SEPA 009), sorbitan monolaurate (Span20), and dodecyl-2-dimethylaminopropanoate (DDAIP), which may be provided at a weight/weight concentration of from about 0.1% to about 10%, usually from about 2.5% to about 7.5%, more usually about 5%. Transdermal patches may further comprise additives to prevent crystallization.

EXPERIMENTAL

The following examples are put forth so as to provide those of ordinary skill in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

A targeted approach for the management of the plantar lesions of epidermolysis bullosa simplex (EBS) is provided, by treating blistering/callus lesions on the soles of feet with sirolimus (Rapamycin) as a topical agent.

Sirolimus 2% ointment, has been shown to reduce expression of keratin (KRT) 6/16 and improve walking ability in pachyonychia congenita. A prospective, double-blind, randomized, placebo-controlled, crossover study determines effects on the paired KRT 5/14 which are affected in EBS.

Participants are assigned to treat both feet with either topical sirolimus 2% ointment twice daily or placebo (vehicle-control) for 12 weeks followed by a washout period of four weeks, then retreatment to both feet with the switched intervention followed by a washout period of four weeks, and then a post-study phone call at 8 weeks thereafter.

This study exploits the naturally occurring transcriptional regulation of keratin sequences, the known gene aberration causing EBS, and assesses mTOR pathway inhibition in treatment of EB patient's plantar lesions. Topical sirolimus 2% selectively blocks 5'oligopyrimidine (TOP) mRNA translation thereby altering mRNAs 5'TOP motifs (Raught et al., 2001). Published sequence data suggest KRT5 mRNA, but not KRT14 mRNA, contain the 5'TOP motif (Hickerson et al., 2009) and thus are viable drug targets of mTOR for the treatment of EBS variants.

We believe that the mTOR inhibitor sirolimus downregulates the translation of defective KRT5 protein and inhibit rapid proliferation of cells that carry the defective keratin, therefore ameliorating the severity of EBS in patients affected. Additionally, altering the mTOR pathway may directly affect pain and itch. Itch and pain are two of the three top symptoms that matter to patients living with EB, both of which are secondary outcome measures in this study.

Aim 1: To assess the safety of topical sirolimus for plantar lesions in the treatment of epidermolysis bullosa simplex (EBS).

Aim 2: To assess the efficacy of topical sirolimus to improve the clinical severity of lesional skin, including pain, in the majority of participants with EBS at the end of treatment versus baseline and compared to an intra-subject control site.

Aim 3: To assess improvement in walking ability and quality of life.

This research study is expected to take approximately 40 weeks. There will be 2 different parts of the study which a subject may receive either (a) placebo (no drug) for 12 weeks or (b) study drug for 12 weeks, during enrollment in the 40 week study. After the initial 12-week period, there will be a washout period before starting treatment again for part 2, and a switch will occur to receive either the placebo or study drug depending on which was received first. At some time point during the 40-week study, at least both feet will get study drug. There will also be a post treatment visit at week 16 and week 32, with a post study phone call at Week 40. The last study visit will be at week 32 with a last study phone call occurring at week 40.

The EBDASI feet score needs to be within 20% of baseline to progress to Phase 3. If it does not meet this criteria the Phase 2 wash-out can be extended to 6 weeks. Treatments are switched after Phase 2. Structured physician phone-call will be scheduled at Week 14 and week 40.

Preference in enrolment will be given to participants in proximity to the study site and those with genetic KRT 5/14 mutations. Genetic testing is not a requirement for EBS diagnoses nor study enrollment. The mechanism of disease in EBS is well known as an autosomal dominant defect in keratin 5 or keratin 14. We have genotype information of most participants. The test has been performed on some of the patients, as the cost of genotyping is high at $3-4 k per subject. If genotyping is already known, this information will be utilized.

Participants who meet all eligibility criteria will be randomized 1:1 to receive either topical sirolimus 2% or placebo ointment. The on-site Registered Nurse will teach the participant how to apply the ointment to both feet and will administer the first dose of IMP at week 0. Subsequent twice daily application of IMP to both feet will be performed by the participant, this will continue for 12 weeks.

After completion of Phase 1 the participant will stop applying the IMP to the feet for a period of 4 weeks at which point their baseline activity will be assessed. If their EBDASI feet score is within 20% of baseline they can proceed to Phase 3.

Participants who received topical sirolimus 2% during phase 1 will switch to placebo ointment and vice versa. Twice daily application of IMP will be continued by the participant for a further 12 weeks. The trial will remain double-blinded throughout.

After completion of Phase 3 participants will enter a further 4-week wash-out period where they will stop applying the IMP to their feet. At the end of Phase 4 they will attend for their final end-of-trial physician visit.

Week 32-40 will be the follow-up period with a structured physician phone consultation at Week 40. Participants who withdraw from treatment will also enter the follow-up period.

Topical sirolimus 2% and placebo ointment will be made and supplied by PCCA compounding pharmacy. Placebo ointment will consist of vehicle only—i.e. all the same components as the topical sirolimus 2% ointment minus the active ingredient. Both will have the same appearance, texture and odor and will be in a matching container or tube.

Tubes will contain vehicle or sirolimus 2% ointment in a 60 gram supply, the amount of topical for twice daily application over 2 weeks. We expect 360 grams for each phase of the treatment, 720 grams total with 360 grams intervention and 360 grams vehicle. Vehicle is an ointment plasticized base containing no water that provides at least 6 months sirolimus stability (Chemistry RX, Lars Brichta April 8 communication; PCCA plasticized base information provided in Section 16). 'A kit' describes two components in a plastic bag or cardboard box: (1) vehicle (placebo) or intervention (sirolimus 2%) ointment in 60 gram tubes and (2) our "Study Drug Application Kit Instructions" (provided in Section 16).

This is a double-blind study. All study staff (which includes the investigator, sub-investigators, other site staff) and participants will be blinded to the treatment allocation throughout the trial. The blinded study treatment assignments for individual participants will be maintained by a Central System. Emergency unblinding will be available via the central system in a case where the identity of the IMP must be known in order to treat an emergent adverse experience for an individual patient. If the treatment blind is broken for a participant in the treatment period, the participant in question will be withdrawn from the treatment period and moved into the follow-up period. During the study, investigators will not receive central laboratory data that have the potential to unblind a subject's treatment assignment.

Primary outcome measurements. Foot function utilizing the validated Foot Health Status Questionnaire (FHSQ) as a change from baseline to the end of each treatment. Safety and tolerability of topical sirolimus 2% ointment (serum trough sirolimus levels, monitoring for adverse events).

Secondary Outcome Measures. Plantar defect size measurements using 3D photography (% change in total defect area) from baseline to the end of each treatment. EB Disease Activity and Scarring Index (EBDASI) feet activity scores as a change from baseline to the end of each treatment. Quality of life assessment in EB (QOLEB) as a change from baseline to the end of each treatment. Itch severity measured using 5-D Pruritus Scale as a change from baseline to the end of each treatment. Participants will wear a FitBit® for the duration of the study to assess number of steps walked per day as a change from baseline to the end of each treatment. Changes in foot plantar pressure measurements before and after treatment using the Podotech Elftman Foot Scanner from baseline to the end of each treatment. Molecular biology study of skin biopsies assayed for mTOR pathway inhibition (e.g. determination of phosphoprotein inhibition included ribosomal protein S6, S6 kinase and/or eIF-4E binding protein) as a change from baseline to the end of each treatment.

The EBDASI is a validated scoring system that objectively quantifies the severity of EB affecting the entire body. It has been designed to evaluate the response to new therapies for the treatment of EB. It was developed and validated many time over in the literature (Loh et al., 2014)

EBDASI feet score is a subsection of the EBDASI and objectively quantifies activity and damage levels relating to the feet only. Activity is graded according to size and number of lesions (blisters/erosions) in specific anatomical area. Damage is graded according to the presence/absence of the following signs: erythema, pigmentation, poikiloderma, atrophy, hyperkeratosis, scarring and milia. Tracing of affected wounds will be performed using Visitrak Digital Wound Assessment System. This is a portable device that provides accurate, reproducible data for tracking wound progress.

QOLEB is a Quality of Life Questionnaire specifically designed for people with EB. The QOLEB can be used to identify everyday life occurrences negatively affected by EB. It assesses change in quality of life over time, an important measure when assessing the success of new treatments for EB (Frew et al., 2009).

Each enrolled study subject will receive a FitBit®/pedometer during their participation in the study to track their activity levels. The FitBit/pedometer will sync stats wirelessly. FitBit pedometers have been demonstrated in the literature as reliable and accurate (Storm F A et al. Step Detection and Activity Recognition Accuracy of Seven Physical Activity Monitors. PLoS ONE, 2015).

The skin biopsies will be assayed for transcriptional factors of mTOR pathway inhibition using Western blot/immunohistochemical methods (Transderm laboratory, Santa Cruz USA) e.g. determination of phosphoprotein inhibition included ribosomal protein S6, S6 kinase and/or elF-4E binding protein. Tissue samples will be transferred to Transderm laboratory deidentified and without identifiable personal health information.

People with EBS can experience the aggravating symptom of itch. This validated tool will be utilized to assess the effect (if any) topical sirolimus has on this symptom (Elman
Fine, Jo-David, et al. "Inherited epidermolysis bullosa: updated recommendations on diagnosis and classification." *Journal of the American Academy of Dermatology* 70.6 (2014): 1103-1126.
Fine, J-D., et al. "Assessment of mobility, activities and pain in different subtypes of epidermolysis bullosa." *Clinical and experimental dermatology* 29.2 (2004): 122-127.
Lane, E. B., and W. H. I. McLean. "Keratins and skin disorders." *The Journal of pathology* 204.4 (2004): 355-366.
Castedo, M., K. F. Ferri, and G. Kroemer. "Mammalian target of rapamycin (mTOR): pro- and anti-apoptotic." *Cell death and differentiation* 9.2 (2002): 99-100.
Guba, Markus, et al. "Rapamycin inhibits primary and metastatic tumor growth by antiangiogenesis: involvement of vascular endothelial growth factor." *Nature medicine* 8.2 (2002): 128-135.
Fogel, Alexander L., Sharleen Hill, and Joyce M C Teng. "Advances in the therapeutic use of mammalian target of rapamycin (mTOR) inhibitors in dermatology." *Journal of the American Academy of Dermatology* 72.5 (2015): 879-889.
Raught, Brian, Anne-Claude Gingras, and Nahum Sonenberg. "The target of rapamycin (TOR) proteins." *Proceedings of the National Academy of Sciences of the United States of America* 98.13 (2001): 7037.
Hickerson, Robyn P., et al. "Rapamycin selectively inhibits expression of an inducible keratin (K6a) in human keratinocytes and improves symptoms in pachyonychia congenita patients." *Journal of dermatological science* 56.2 (2009): 82-88.
Roger Kaspar PhD TransDerm Inc www.clinicaltrials.gov: Topical Sirolimus for the Treatment of Pachyonychia Congenita (PC)
Riskowski, Jody L., Thomas J. Hagedorn, and Marian T. Hannan. "Measures of foot function, foot health, and foot pain: American Academy of Orthopedic Surgeons Lower Limb Outcomes Assessment: Foot and Ankle Module (AAOS-FAM), Bristol Foot Score (BFS), Revised Foot Function Index (FFI-R), Foot Health Status Questionnaire (FHSQ), Manchester Foot Pain and Disability Index (MFPDI), Podiatric Health Questionnaire (PHQ), and Rowan Foot Pain Assessment (ROFPAQ)." *Arthritis care & research* 63.S11 (2011): S229-S239.
Loh, Clement C H, et al. "Development, reliability, and validity of a novel Epidermolysis Bullosa Disease Activity and Scarring Index (EBDASI)."*Journal of the American Academy of Dermatology* 70.1 (2014): 89-97.
Venugopal, Supriya S., et al. "A phase II randomized vehicle-controlled trial of intradermal allogeneic fibroblasts for recessive dystrophic epidermolysis bullosa." *Journal of the American Academy of Dermatology* 69.6 (2013): 898-908.
Frew, J. W., et al. "Quality of life evaluation in epidermolysis bullosa (EB) through the development of the QOLEB questionnaire: an EB-specific quality of life instrument." *British Journal of Dermatology* 161.6 (2009): 1323-1330.
Elman, S., et al. "The 5-D itch scale: a new measure of pruritus." *British Journal of Dermatology* 162.3 (2010): 587-593.
Storm F A et al. Step Detection and Activity Recognition Accuracy of Seven Physical Activity Monitors. *PLoS ONE,* 2015

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements, and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for the targeted treatment of Epidermolysis Bullosa simplex (EBS) caused by a genetic mutation in one or both of keratin K5 and keratin K14, to improve clinical severity of lesional skin, the method comprising
contacting topically a lesion of a patient suffering from EBS with an effective dose of a formulation comprising 0.1% to 5% rapamycin.

2. The method of claim 1, wherein the lesion is a plantar lesion.

3. The method of claim 1, wherein the formulation comprises a dose equivalent to about 2% rapamycin.

4. The method of claim 1, where the individual has been genotyped for a mutation in one or both of K5 and K14.

5. The method of claim 1, wherein the individual is monitored for one or more indicia of effectiveness.

6. The method of claim 5, wherein the indicia of effectiveness are selected from foot function utilizing the validated Foot Health Status Questionnaire (FHSQ) as a change from baseline to the end of each treatment; a decrease in plantar defect size measurements; a change in EB Disease Activity and Scarring Index (EBDASI) feet activity scores; improved quality of life assessment in EB (QOLEB); reduced itch severity; increased mobility; and mTOR pathway inhibition.

7. A method for the targeted treatment of Epidermolysis Bullosa simplex (EBS) to improve clinical severity of lesional skin, the method comprising:
contacting topically once or twice daily a lesion of a patient suffering from EBS with an effective dose of a formulation comprising 0.1% to 5% of rapamycin or a rapamycin analog selected from CCI-779, Everolimus, and ABT-578.

8. The method of claim 1, wherein the lesion is a plantar lesion.

9. The method of claim 7, wherein the formulation comprises a dose equivalent to about 2% rapamycin.

10. The method of claim 7, wherein the individual is monitored for one or more indicia of effectiveness.

11. The method of claim 10, wherein the indicia of effectiveness are selected from foot function utilizing the validated Foot Health Status Questionnaire (FHSQ) as a change from baseline to the end of each treatment; a decrease in thickness of keratoderma on the feet; a change in EB Disease Activity and Scarring Index (EBDASI) feet activity scores; improved quality of life assessment in EB (QOLEB); reduced itch severity; increased mobility; and mTOR pathway inhibition.

12. A method for the targeted treatment of a patient with Epidermolysis Bullosa simplex (EBS) caused by a genetic mutation in keratin K5 or keratin K14 to reduce pain, thickness of skin on plantar surface and improve function of feet and ambulation, the method comprising:
contacting topically once or twice daily a plantar lesion of the patient suffering from EBS with an effective dose of a formulation comprising 1% to 4% rapamycin once or twice daily for a period of at least 12 weeks.

* * * * *